US009285336B2

(12) United States Patent
Gupta

(10) Patent No.: US 9,285,336 B2
(45) Date of Patent: Mar. 15, 2016

(54) SENSING PLATFORM FOR QUANTUM TRANSDUCTION OF CHEMICAL INFORMATION

(71) Applicant: The Board of Trustees of the Leland Stanford Junior University, Palo Alto, CA (US)

(72) Inventor: Chaitanya Gupta, Foster City, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 209 days.

(21) Appl. No.: 13/963,272

(22) Filed: Aug. 9, 2013

(65) Prior Publication Data
US 2014/0043049 A1 Feb. 13, 2014

Related U.S. Application Data

(60) Provisional application No. 61/681,380, filed on Aug. 9, 2012.

(51) Int. Cl.
G01R 27/26 (2006.01)
G01N 27/414 (2006.01)
B82Y 15/00 (2011.01)
G01N 33/561 (2006.01)
G01N 33/68 (2006.01)

(52) U.S. Cl.
CPC ............ *G01N 27/4145* (2013.01); *B82Y 15/00* (2013.01); *G01N 27/4148* (2013.01); *G01N 33/561* (2013.01); *G01N 33/6803* (2013.01)

(58) Field of Classification Search
CPC .......... G01N 27/3271; G01N 27/3276; G01N 32/3278
USPC ........................................ 324/693, 698, 71.1
See application file for complete search history.

(56) References Cited

U.S. PATENT DOCUMENTS

2008/0036444 A1* 2/2008 Paulus et al. ................. 324/71.1
2012/0091011 A1* 4/2012 Graham et al. ............... 205/775

* cited by examiner

*Primary Examiner* — Vincent Q Nguyen
(74) *Attorney, Agent, or Firm* — Thomas|Horstemeyer, LLP.

(57) ABSTRACT

A system for determining chemistry of a molecule in a high background interfering liquid environment by application of an electronic signal at a biased metal-electrolyte interface is disclosed. One or more of a resonant exchange of energy between one or more electrons exchanged by the metal and the electrolyte and vibrating bonds of a molecular analyte, for example, may be sensed by measuring small signal conductivity of an electrochemical interface.

20 Claims, 16 Drawing Sheets

| Objective Description | Metric |
|---|---|
| Transition current magnitude | 10fA |
| Noise in measured current | $2fA/Hz^{1/2}$ |
| BoNT-A concentration in serum | 1pM |
| Staph. ent-B concentration in serum | 20pM |
| TNF-α concentration in serum | 5pM |
| IL-1 concentration in serum | 5pM |
| IFN-γ concentration in serum | 5pM |

FIG. 14

SENSING PLATFORM FOR QUANTUM TRANSDUCTION OF CHEMICAL INFORMATION

CROSS-REFERENCE TO RELATED APPLICATIONS

This application claims the benefit of U.S. Provisional Application No. 61/681,380, filed Aug. 9, 2012, the entire contents of which is hereby incorporated herein by reference.

STATEMENT REGARDING FEDERALLY SPONSORED RESEARCH OR DEVELOPMENT

This invention was made with government support under contract N66001-11-1-4111 awarded by the Defense Advanced Research Projects Agency. The government has certain rights in this invention.

BACKGROUND

Identification and analysis of chemical and molecular species within an environment is well established. Typically, electronic systems rely upon alterations in current, voltage, or charge to indirectly qualify and quantify chemical analytes. Bioassays detect analytes indirectly by measuring various molecular interactions. Some bioassays measure analytes by activating a label that is covalently attached to a binding partner, upon analyte binding to a bait molecule. Other bioassays measure analyte binding to an immobilized bait molecule to a solid substrate and measuring changes in charge, refractive index, or mass change at an interface between the solid substrate and liquid sample. Demand for a low-cost and field-use friendly method of low concentration analytes has resulted in ongoing efforts to improve the functionality and practicality of chemical and molecular detecting devices.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 14 shows a table containing program metrics.

DETAILED DESCRIPTION OF THE EMBODIMENTS

Figure 1A:
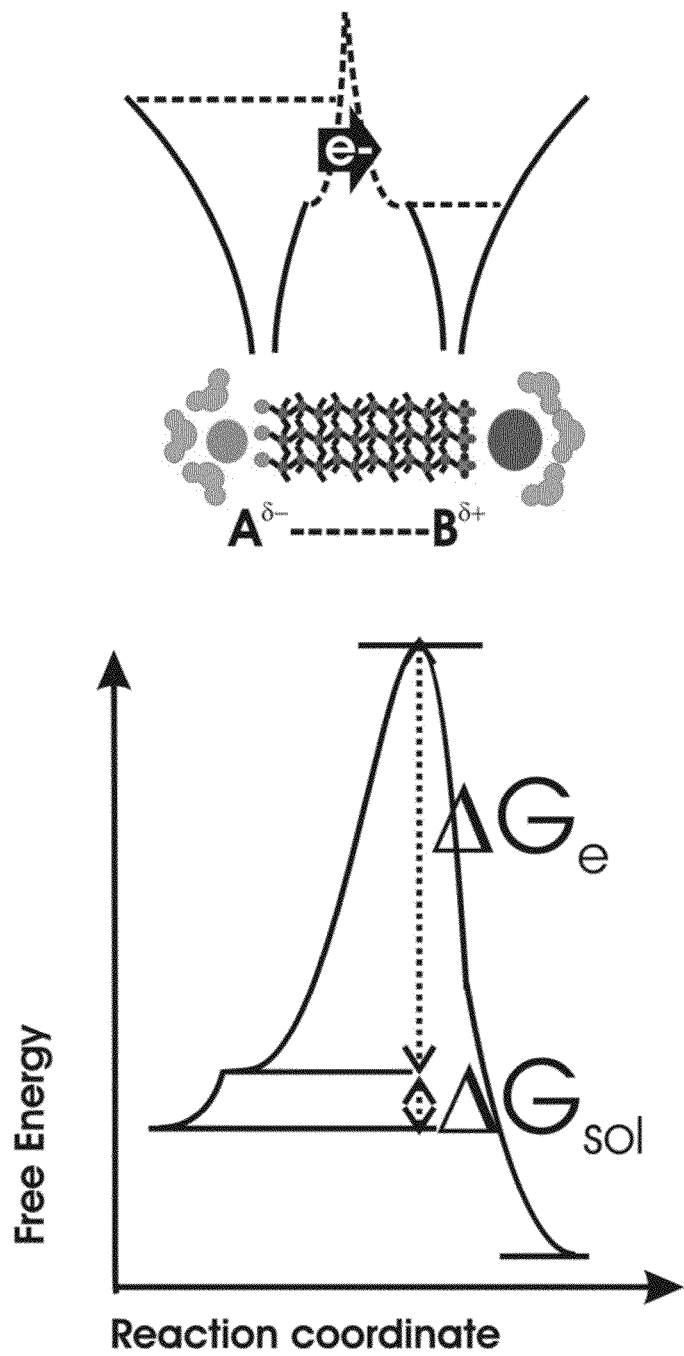
FIG. 1A shows transition states of a nonadiabatic reaction.

Reference is now made in detail to the description of the embodiments as illustrated in the drawings. While several embodiments are described in connections with these drawings, the disclosure is not intended to be limited to the embodiment or embodiments disclosed herein. On the contrary, the intent is to cover all alternatives, modifications, and equivalents.

For a variety of applications, detection and identification of small amounts of various molecules is desired. Typical molecular species whose detection is desired include, but is not limited to, small molecule analytes like amino acids and metallic ions to large biological like proteins, DNA, and RNA. In particular, detection of biomarkers in biological samples is important for disease detection, disease analysis, and disease pathway investigation. Further, detection of contaminants in environmental samples, such as water, is important for homeland security, public safety, and environmental welfare.

For example, an ideal platform for use in detecting biological threats should be well suited to identifying a large range of harmful agents and toxins. As many of these agents and toxins are highly infective, the platform must demonstrate great sensitivity and specificity to allow early exposure detection, reduce false positives, and enable targeted countermeasures and minimize spread of infection. The platform must also allow for rapid detection to enable timely intervention. The challenge of developing a sensitive, yet specific, high throughput detector with a large working range may be appreciated. The challenges are complicated by a need for the detector to be portable and have minimal operational complexity, low power consumption, low manufacturing cost, and operability in harsh environments.

Platforms for detecting molecules in samples have evolved over the years, from purely laboratory based and impractical for point-of-use detection, to portable miniaturized "Lab-on-a-Chip" platforms. For example, detection of biological threats has evolved from conducting threat detection and diagnosis though Laboratory Response Network, to a mobile lab based system, such as Biological Integrated Detection System (BIDS), to mesoscale peptide bioassays. This evolution is a direct reflection of the need for small molecule detectors that are capable of rapid and point-of-use detection.

Traditional bioassays fall into two categories: label-based or label-free. In label-based bioassays, the target molecule, such as a toxin, binds with a bait molecule, often a complementary peptide, DNA, or RNA molecule, which has a covalently attached label. Fluorescent dyes and radioactive isotopes are commonly used labels where binding of the target molecule to the bait molecule causes the release of fluorescence or radiation. Measurement of fluorescence or radioactivity provides an indirect detection and quantification of the target molecule.

These array label-based assays suffer from significant limitations despite improved sensitivity and specificity. First, these array label-based systems require identification, design, synthesis and immobilization of the bait molecules, which are significantly rate-limiting in the assay manufacturing process. Second, immobilization of a bait molecule with a complex three-dimensional structure results in a loss of activity of the bait molecule, which generates false negative outcomes. Third, the addition of a covalently bound fluorophore or radioactive tag significantly modifies an interaction between the target molecule and the bait molecule, resulting in false positives and negatives. Fourth, tagging a bait molecule with a fluorescing or radioactive label adds a layer of complexity to the manufacturing process. Fifth, the assay requires that readers to detect the optical/radiation signal from the tags be incorporated with the platform, thus dramatically increasing platform cost and reducing platform portability. Finally, extinction of a signal generated from a binding event due to scattering from the background matrix is a persistent problem resulting in low signal-to-noise.

The limitations imposed by traditional labeled bioassays prompted the development of the label free methods. Like the label-based assay, the label free assay is array based with bait molecules immobilized on a solid substrate. The detection of the binding between the target molecule and bait molecule is based on (a) the change in charge at the solid-liquid interface that results from the binding event, (b) evanescent waves attenuation due to a change in refractive index at the solid-liquid interface, or (c) mass change at the solid-liquid interface. Charge based detection methods eliminate the need for expensive signal readers, thereby reducing the cost of detection, enhancing system portability, reducing overall power consumption, and increasing ease of operation. The charge based method is also scalable, which is an essential strategy in developing a high throughput detection platform. Though the label-free platforms do not suffer from problems like tag-altered target molecule binding and reduced signal yield, they are still afflicted by the issue of bait molecule misfolding on immobilization to a solid surface.

The bait molecule is utilized to infer whether the target molecule is present or absent in both label-based and label-free platforms. The actual identity of the target molecule is inferred from the nature of the bait molecule with which binding occurs. Mass spectrometry, on the other hand, is a time-critical, broadband analysis technique that directly measures molecular composition from estimates of charge-to-mass ratios of vaporized fragments of the analyte. Commercial mass spectrometers are reportedly capable of detection in the nanomolar concentration range. Arrayed, multi-channel, modular architectures for time-of-flight (TOF) mass spectrometers have been detailed for rapid, in-parallel acquisition of information.

However, mass spectrometry analysis is better suited to larger molecular weight target molecules that can be fragmented into several constituent moieties for analysis. Small molecular weight (<5 kDa) target molecules are not easily identified by this technique. The mass spectrometer and associated ancillary equipment (like vacuum pumps) are energy intensive in operation and are not easily miniaturized, thus making portability an issue. Additionally, mass spectrometer operation and data analysis require intervention of skilled technicians, making the detection platform ill-suited for point-of-use applications. Thus, in view of traditional detection systems, one of ordinary skill in the art will appreciate the need for a robust, rapid, low-cost, point-of-use detection platform for small amounts of molecules in fluid samples.

Molecular vibration-assisted-charge transfer between electron source in response to a molecule has been documented in nature. Fruit flies detect odorants by transferring an electron from an intracellular electron source upon entrance of an odorant into a transmembrane pocket. The electron charge transfer stimulates G-protein mediated signal transduction pathways and thus allows the fruit fly to identify an odorant. Similarly, according to the embodiments described herein, detection of molecular analytes by detection of an electron transfer is achieved. In the biosensor according to the embodiments described herein, current measured due to electron transfer that contains information about vibrational frequencies of molecular bond vibrations within a molecular analyte is acquired directly from a physical transducing interface and analyzed thereafter.

Generally, the biosensor system according to the embodiments described herein comprises an electrochemical charge transfer platform configured to be "slow", relative to a speed of molecular vibrations of molecules in a liquid sample. This electrochemical charge transfer platform comprises a metal layer and an electrochemical interface separated by a dielectric layer. The electrochemical interface interacts with an electrolyte, or diffuse, layer, which comprises the liquid sample. The dielectric layer acts as a molecular insulator to slow down the rate of electron transfer. The biosensor system further comprises a high gain noise suppression feedback loop to electronically "cool" the system and minimize thermal noise that may otherwise destroy a signal of interest. At low electronic temperatures, transfer of electronic charge occurs in a resonant manner by quantized vibrations of a target analyte. The system measures resonant interactions by measuring small signal conductance across the electrochemical interface. Each resonance, detected on a conductance profile, is correlated to a vibrational frequency of a molecular bond in the analyte. As vibrational frequencies are characteristic signatures of molecular bonds, akin to human fingerprints, the number and types of bonds in the analyte can be determined from a conductance profile. Each analyte possesses a unique molecular bond signature, thus allowing direct, highly specific analyte detection.

In one embodiment, a system for sensing chemical information is described. The system includes a sample acquisition zone, a filtration module operatively coupled (e.g., via wicking, etc.) to the sample acquisition zone, an immunoseparation module operatively coupled to the filtration module, a tapered micro-chromatogram operatively coupled to the immunoseparation module, and an adsorption pad operatively coupled to the tapered micro-chromatogram. In one embodiment, the system further includes a quantum tunneling biosensor interface mounted on a shielded printed circuit board, the quantum tunneling biosensor interface being operatively coupled to the adsorption pad. The quantum tunneling biosensor interface may include a transducing electrode array including dielectric thin films deposited on a metal electrode array. The metal electrode array may be layered on a silicon die, and the silicon die may include through-silicon vias. The biosensor interface may further include processing logic operatively coupled to the through-silicon vias.

In another embodiment, a system including a quantum tunneling biosensor interface, a transducing electrode array, and processing logic is described. According to certain aspects, the transducing electrode array may be located on or adjacent to the quantum tunneling biosensor interface. The transducing electrode array includes dielectric thin films layered on a metal electrode array. The metal electrode array may be mounted on a silicon die. The processing logic may be operatively coupled to the transducing electrode array by through-silicon vias in the silicon die.

The system may further include a modular fluidic system. The modular fluidic system may include a sample acquisition zone, a coarse filtration module operatively coupled (e.g., via wicking, etc.) to the sample acquisition zone, an immunoseparation module operatively coupled to the coarse filtration module, a tapered micro-chromatograph operatively coupled to the immunoseparation module, and an adsorption pad operatively coupled to the quantum tunneling biosensor interface.

According to another embodiment, a method of identifying a target analyte in a biological fluid is described. According to various aspects, the method includes applying biological fluid to a dielectric monolayer modified electrochemical interface, applying a voltage bias across the electrochemical interface, and measuring a flux of electronic charge across the electrochemical interface. In certain embodiments, applying a voltage bias across the electrochemical interface may include tuning the voltage bias to achieve a weakly coupled, non-adiabatic electronic transfer across the electrochemical interface. The method may further include filtering the biological fluid prior to applying the biological fluid to the dielectric monolayer modified electrochemical interface, wherein filtering the biological fluid includes passing the biological fluid through a porous membrane resulting in size fractionated fluid.

According to additional aspects, the method may further include passing the size fractionated fluid through a membrane coated with a protein specific antibody resulting in size fractionated and immunoseparated fluid. The method may further include passing the size fractionated and immunoseparated fluid through a micro-chromatograph.

Resonant Electron Transfer at an Electrochemical Interface

The biosensor system according to the embodiments described herein relies upon measuring electron flux or leakage currents produced in non-adiabatic, charge-transfer-related transitions at an electrochemical interface. The leakage currents provide or are representative of high-resolution molecular structural information. The molecular structural information, one determined, is unique to each analyte, thus allowing for highly specific molecular species determination.

Figure 1B:
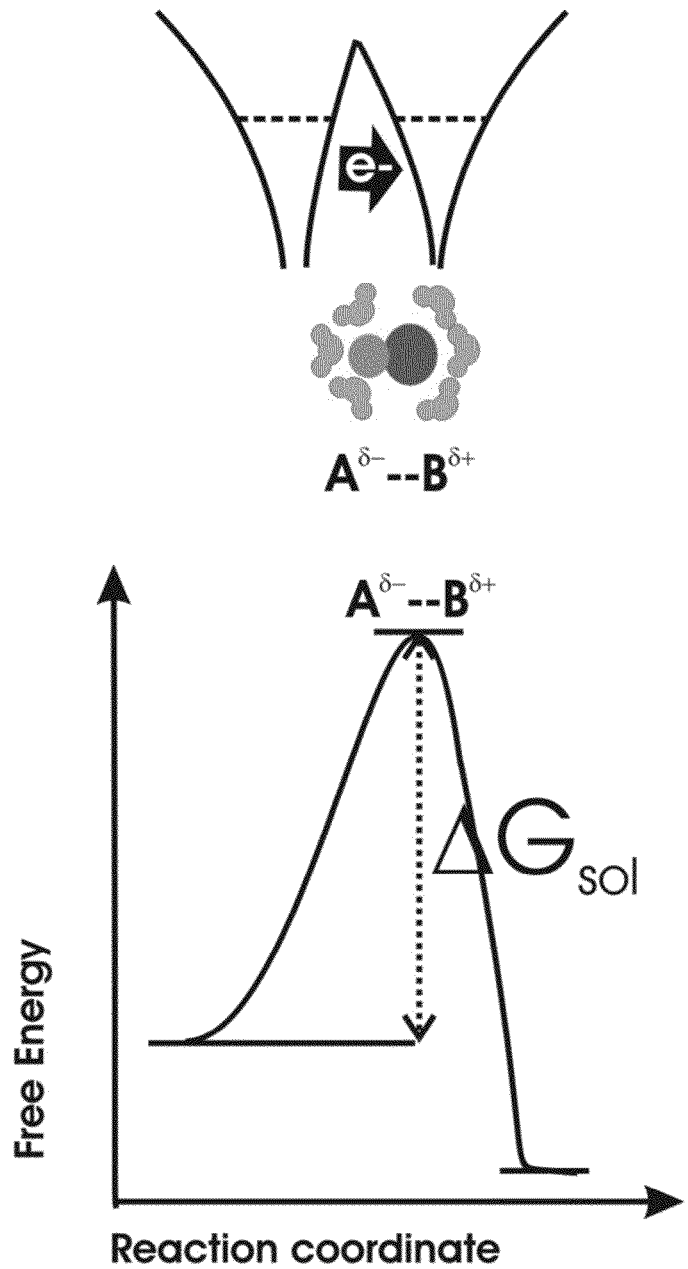
FIG. 1B shows transitions states of an adiabatic reaction.

FIG. 1A shows transition states of a nonadiabatic reaction, and FIG. 1B shows transitions states of an adiabatic reaction. Charge transfer across an electrified electrode-insulator-electrolyte interface is limited by a quantum-mechanical, electron transition process. The nature of the electron transition and the magnitude of the transition charge flux depends on the extent of coupling between the initial and final states of the transferring electron, which can be non-adiabatic, as illustrated in FIG. 1A, or adiabatic, as illustrated in FIG. 1B. Further, a coupling potential energy is a function of a voltage bias applied across the electrochemical interface. Coupling strength can be tuned by changing an applied voltage bias, for example, by tuning a local interface chemistry, by conditioning the system to reduce intrinsic noise, or by scaling down a physical sensor of the system. Coupling potential is determined from electrostatic interactions between transitioning electrons and ionic charges in a double layer at the electrochemical interface, as well as on the electrostatic interactions that occur with a liquid sample bath which cause thermal dephasing of resonance phenomena in the charge transfer process.

Figure 2A:
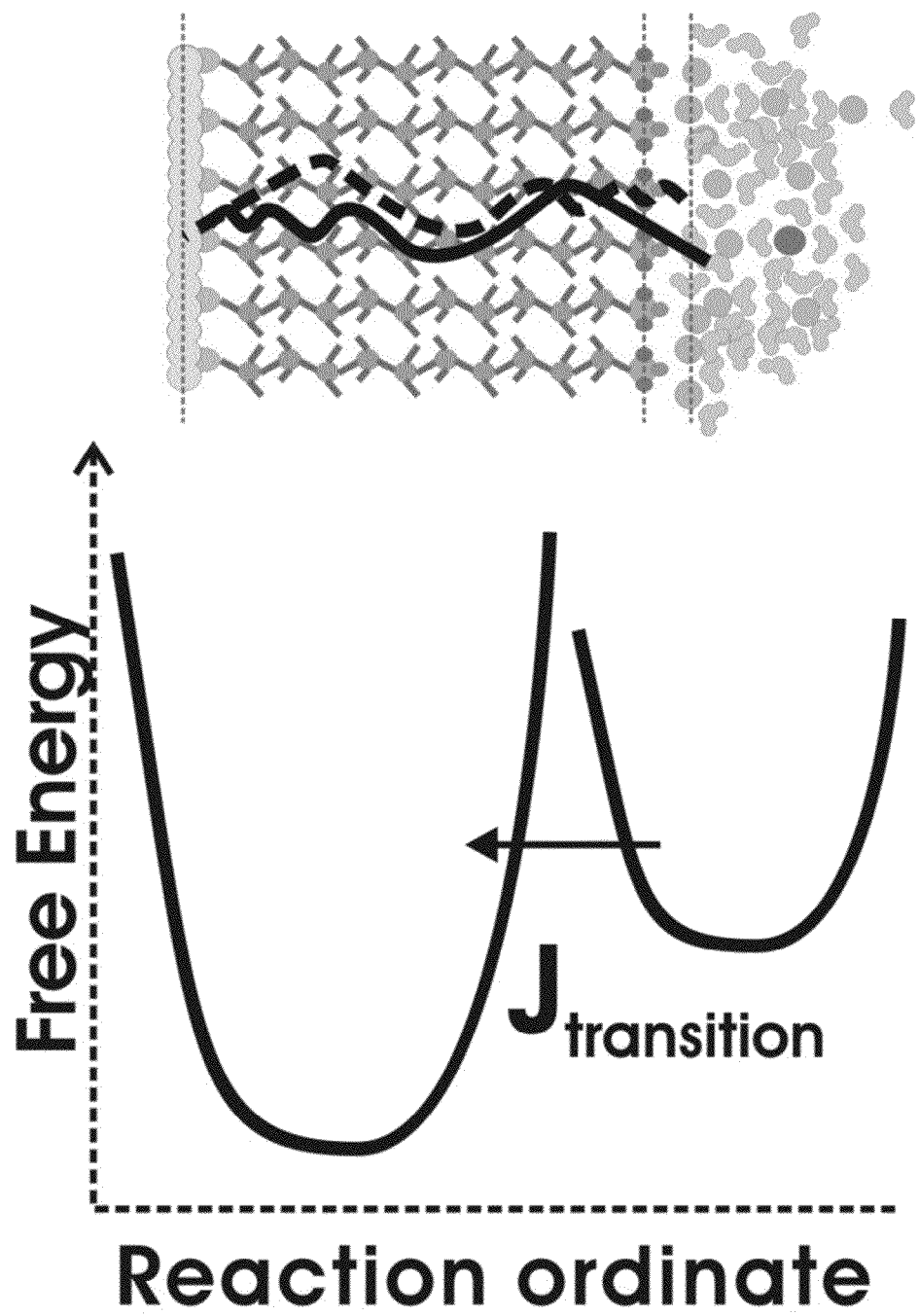
FIG. 2A shows weak coupling between initial and final electronic energy states in the nonadiabatic reaction of FIG. 1A.
Figure 2B:
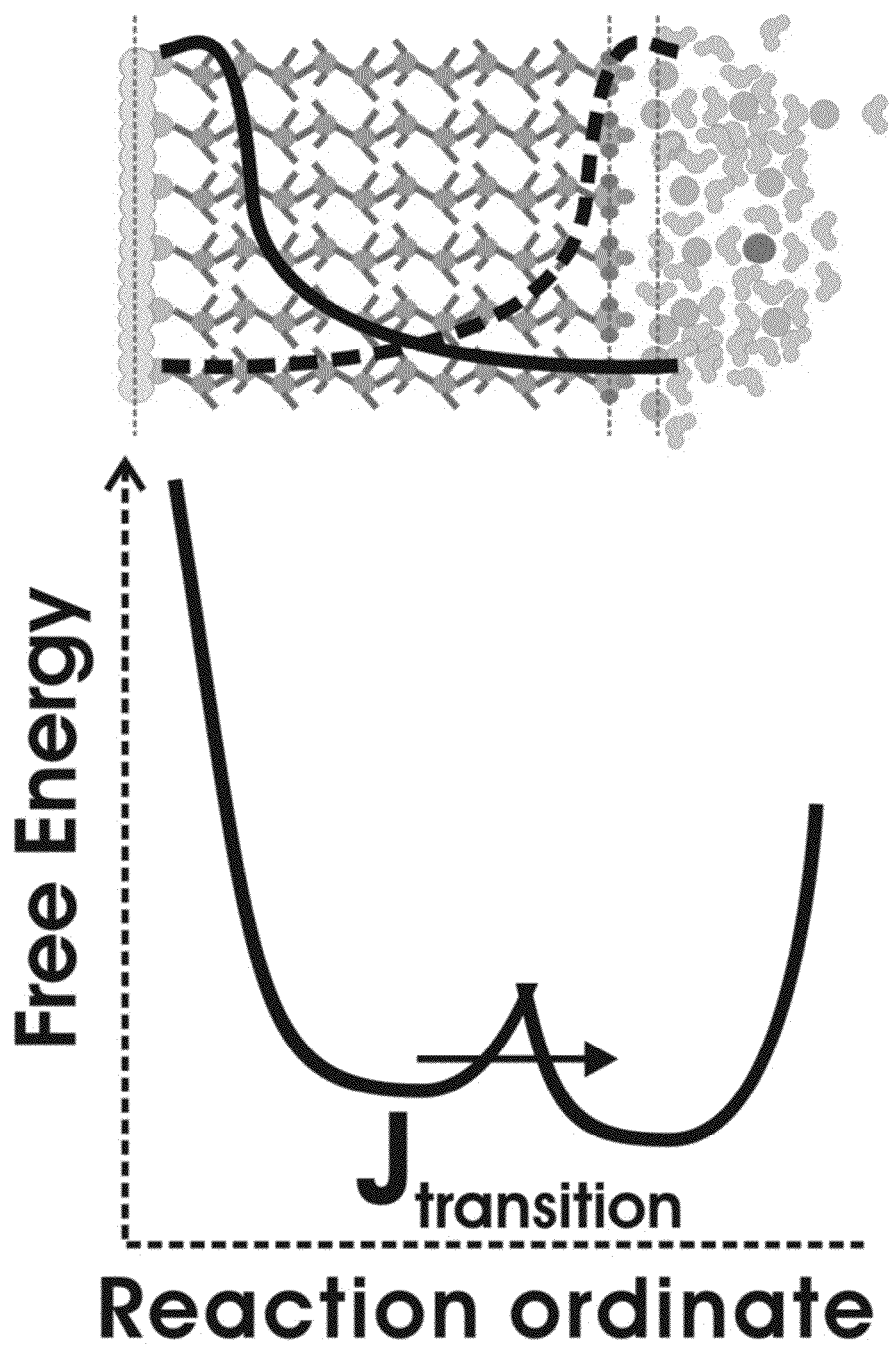
FIG. 2B shows strong coupling between initial and final electronic energy states in the adiabatic reaction of FIG. 1B.

FIG. 2A shows weak coupling between initial and final electronic energy states in the non-adiabatic reaction of FIG. 1A, and FIG. 2B shows strong coupling between initial and final electronic energy states in the adiabatic reaction of FIG. 1B. The coupling between initial and final states can be weak, as illustrated in FIG. 2A, or strong, as illustrated in FIG. 2B, and the coupling strength may be tuned, for example, by applied bias, interface chemistry, interface size and intrinsic interface noise. Where an applied voltage bias allows for an electron transition and initial and final electron energy states are significantly coupled to one another, de-phasing is strong (See FIG. 2B). In a strongly coupled electron transfer, the electron wavefunction is localized to initial and final energy states before and after the charge transition, which results in particle-like behavior and an adiabatic charge transfer. Thus, the charge transfer is "fast" and limited only by the rate of dielectric polarization around a reactant and product species. The transitioning electron is always in a ground state resulting in no possibility for resonant electron transfer to occur.

In contrast, where the applied voltage bias allows for the initial and final energy state of the transferring electron to be weakly coupled to one another in a non-adiabatic reaction, then electron transfer via electron tunneling occurs (See FIG. 2A). In this transition, an electron may be spread over the electrochemical interface as a delocalized wave both before and after energy state transition. Thus, electron transfer is limited by a rate of electron transition from reactant to product state, which is a function of the composition of the intervening dielectric layer. The transition event in this case is tunneling limited. This weakly coupled transition allows a transferring electron to be excited to a higher energy level, unlike the case when electrostatic coupling is strong. This allows for the possibility of an electron transfer that can be resonant (in energy) with molecular vibrational modes between the electrolyte (and analyte contained within) and the metal electrode.

Vibrational Mode Information Transduction Interface

Figure 3:
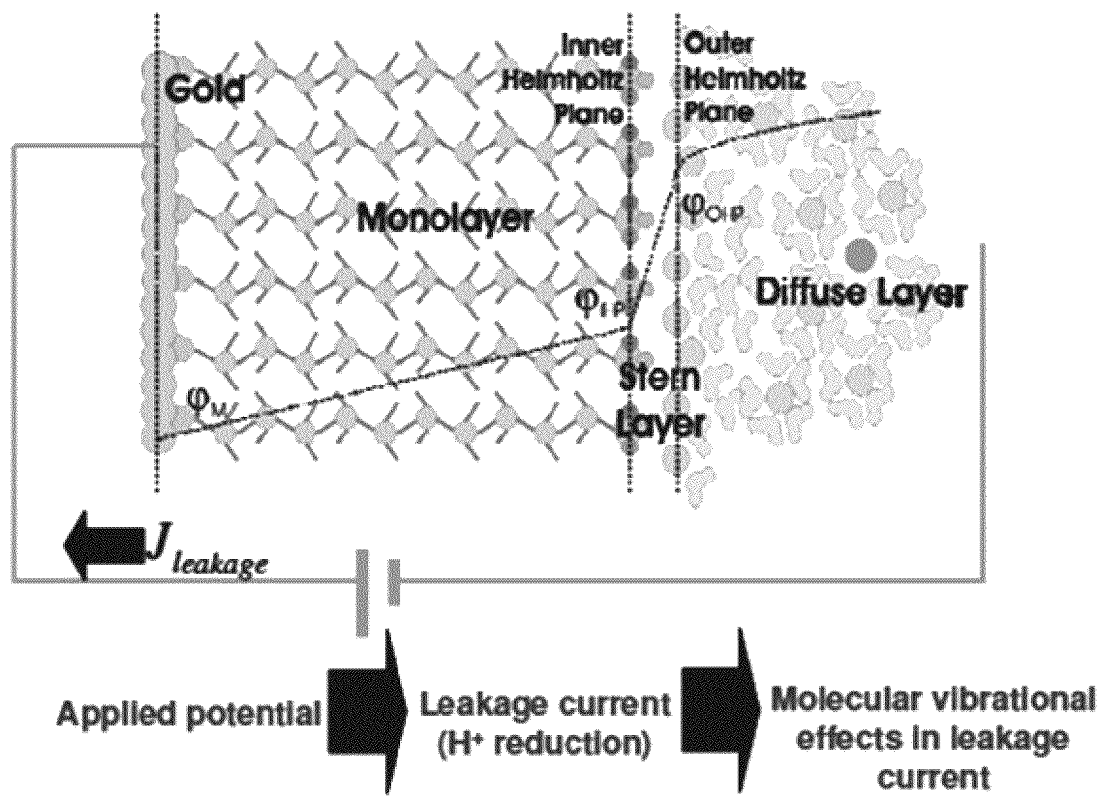
FIG. 3 is a schematic depicting a measurement of a flux of electrons crossing an electrified dielectric monolayer modified electrochemical interface of a biosensor.

The measurement of the flux of electrons ("leakage" currents) crossing an electrified dielectric monolayer modified electrochemical interface allows for analyte detection in the embodiments of the biosensor described herein. In that context, FIG. 3 is a schematic depicting a measurement of a flux of electrons crossing an electrified dielectric monolayer modified electrochemical interface of a biosensor. Leakage currents at electrochemical interfaces have been long ignored through decades of focus on traditional charge-based biosensors. A voltage bias within the weakly coupled bias window is applied to the dielectric monolayer modified electrochemical interface. This results in electronic transfer with a diffuse electron spread across the dielectric monolayer and a resonant energy exchange between quantized energy of the electron-wave and the molecular vibrational modes of analytes in the electrolyte (diffuse) layer. The electron flux or leakage current is measured as an impedance on the system and, by the application of suitable data analysis techniques, detailed structural information about the molecular analyte can be obtained.

Figure 4:
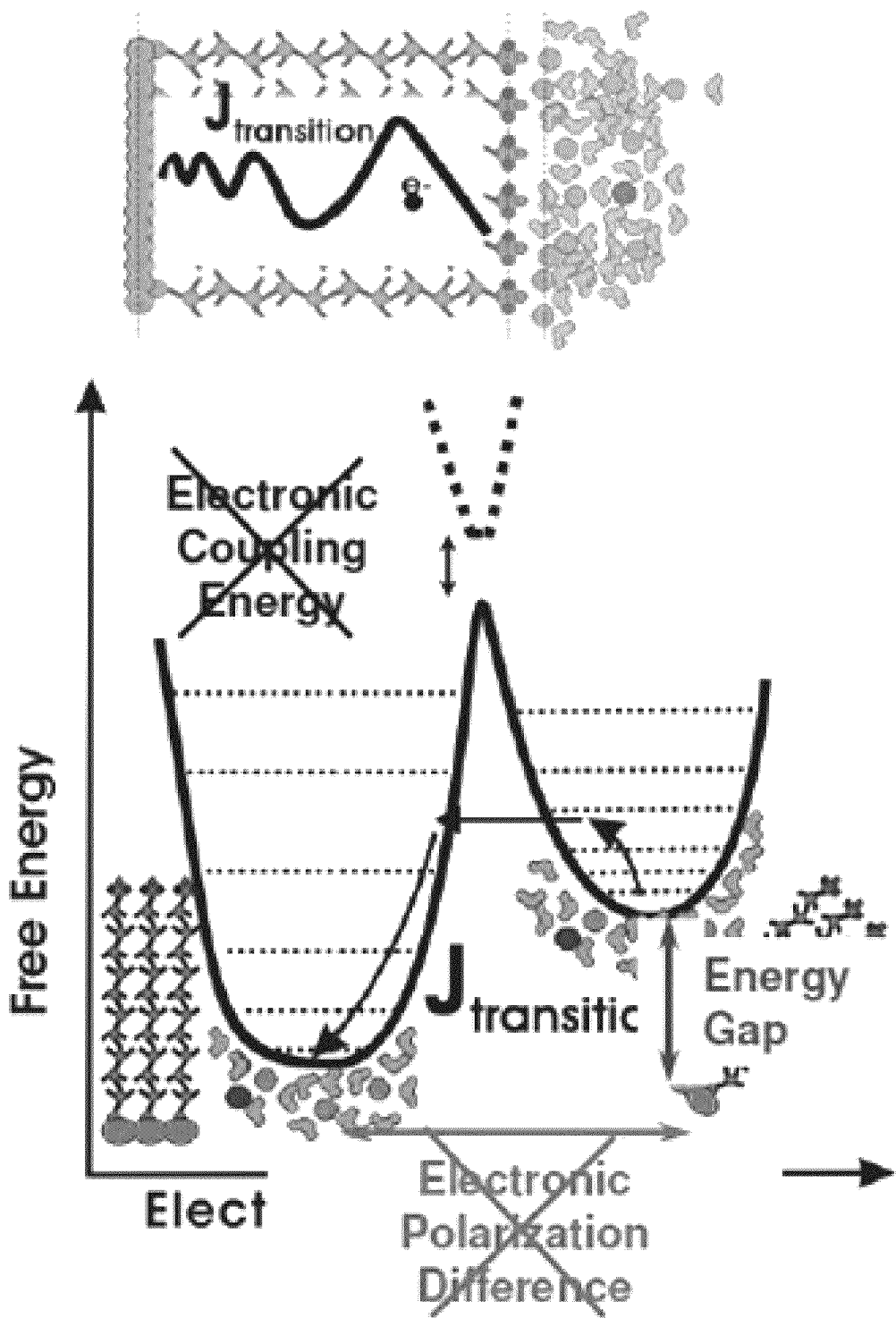
FIG. 4 shows factors affecting energy state transition rate in a weakly coupled, non-adiabatic reaction.

It is noted that, electrochemical charge transfer rate is a function of a rate of quantum-mechanical electron transfer from an analyte in an electrolyte and electrode. In this context, FIG. 4 shows factors affecting energy state transition rate in a weakly coupled, non-adiabatic reaction. The transition rate is determined by electronic polarization difference, electronic coupling energy and energy gap, among other factors. In addition, molecular bonds with vibrations that are resonant with the energy gap excite electron energy state transitions that can be measured as leakage current across the electrochemical interface. Thus, molecular bonds with resonant vibrations can cause leakage currents to flow in addition to background leakage current induced by thermal effects. Thus, the biosensor according to various embodiments described herein measures a spectrum of molecular vibrational oscillation modes of an analyte at an electrochemical interface of a liquid electrolyte that is in resonance with an energy gap limiting the electronic transition potential.

In one sense, this approach has a closer analogy with electromagnetic probes, such as near-infrared (NIR) vibrational spectroscopy, than with conventional electrostatic measurements. However, as molecular structure information is transduced directly to an electronic signal before acquisition, the biosensor according to the embodiments described herein is highly scaleable. The direct acquisition of chemistry specific information about an analyte in the form of molecular vibrational modes also eliminates the need for time and labor-intensive combinatorial screening against bait-molecule probes required by traditional bioassays.

Figure 5:
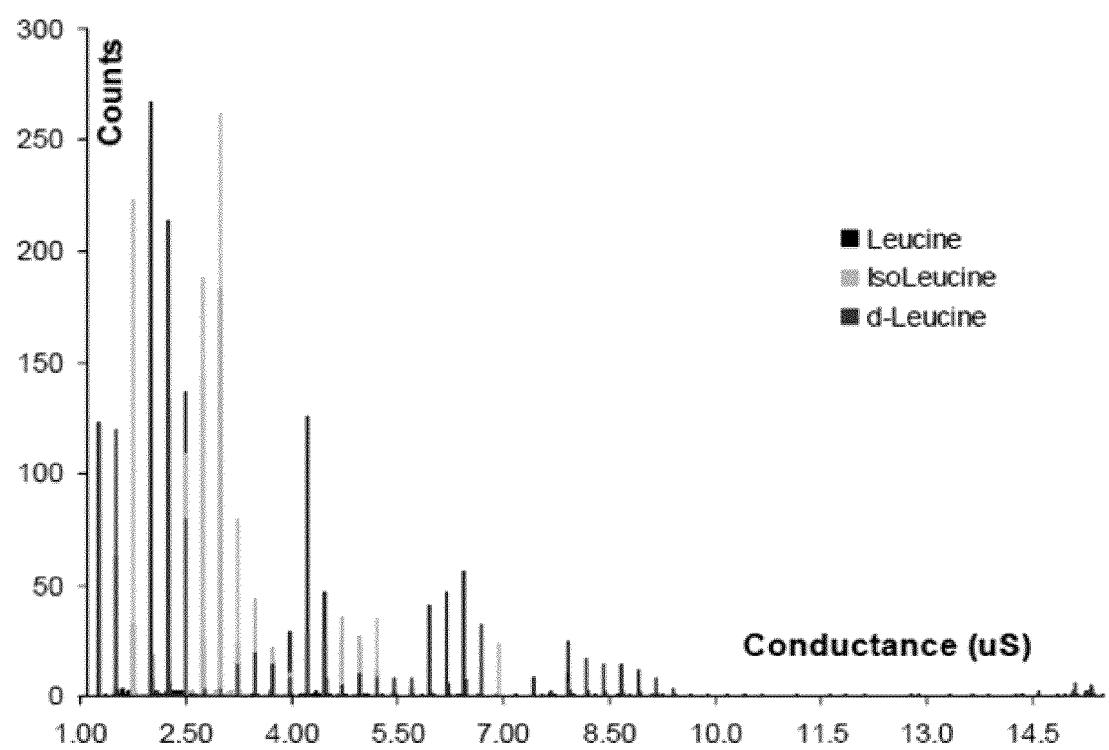
FIG. 5 shows data suggesting sensitivity of the biosensor to a single atom isotope substitution.

A quantum information transduction mechanism described herein enables highly specific interrogation of THz frequency molecular vibrations at experimentally accessible (~mV) electronic energies/potentials, by scanning the electronic energy with an applied voltage at a metallic electrode configure to induce a weak coupling regime. As illustrated in FIG. 5, experimental results suggest sensitivity to a single atom mass isotope substitution and sensitivity to structural isomerism. This sensitivity has not been demonstrated with traditional electronic detection techniques.

Quantum Tunneling Biosensor Platform

In one embodiment, a thin (about 5-10 mm, for example) dielectric-film modified electrode-electrolyte interface is relied upon. The interface may be patterned with windows on a silicon die, where the electrode-electrolyte interface is configured to specifically minimize electronic coupling between electrode and electrolyte phases. Leakage current flux is recorded by low or ultra-low noise acquisition circuitry fabricated, for example, by a complementary metal oxide semiconductor (CMOS) process and integrated with the electrode-electrolyte interface. A shielding and interconnect topology is designed to minimize signal contamination by band-limited noise, electromagnetic interfering signals, flicker noise, detection artifacts, and any residual de-phasing at the electrode-electrolyte interface. Acquired data may be transmitted for further filtering, if necessary, as well as for data recording and display.

In other embodiments, the biosensor may further comprise pre-screening or a means for pre-screening a level of specific biological markers before assaying for an analyte of interest. For example, in a biosensor targeting blood toxins, pre-screening for cytokines allows for evaluation of overall health and can indicate presence or absence of a bacterial infection.

Figure 6:
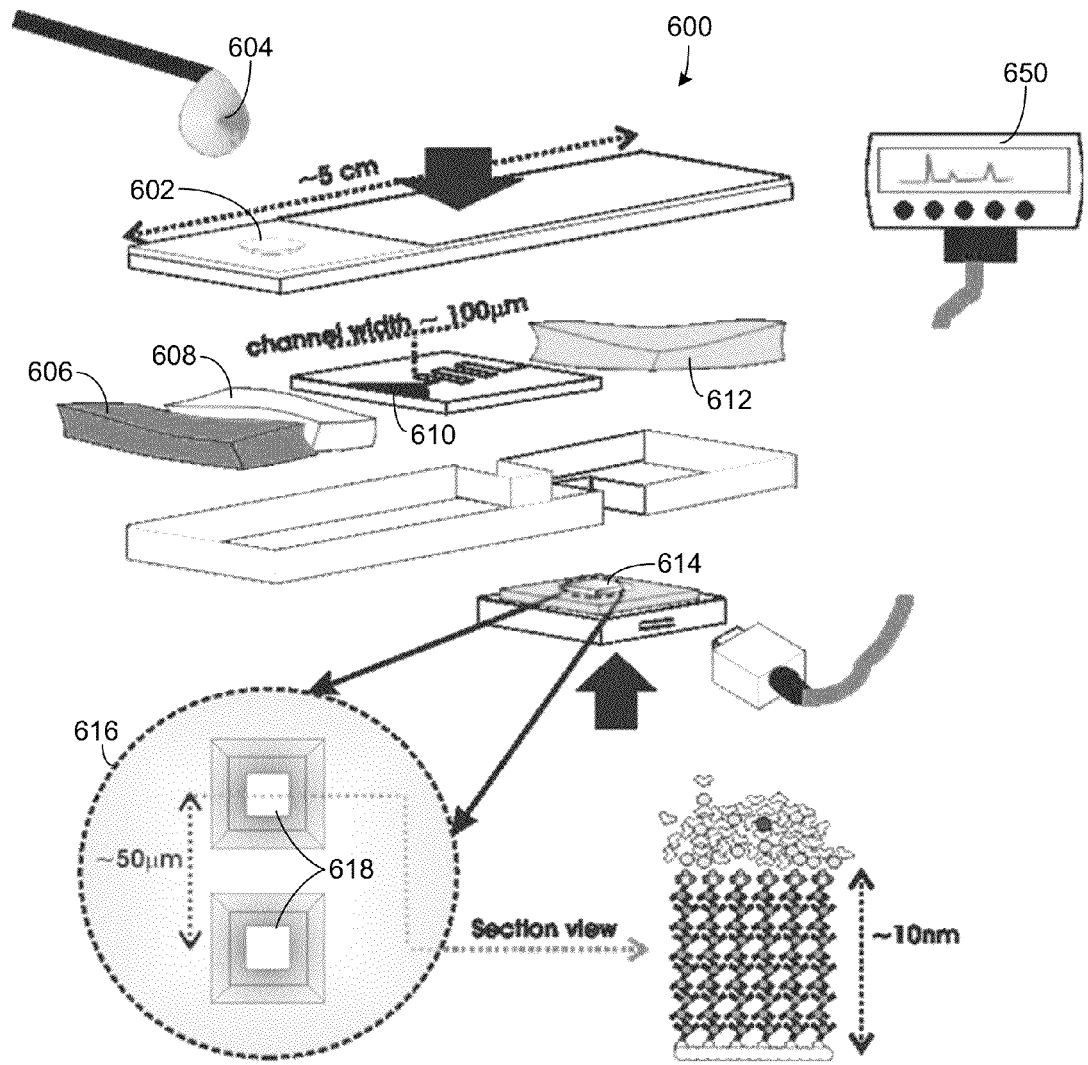
FIG. 6 shows an exemplary embodiment of the biosensor in which a sensor die with a patterned electrochemical interface and a CMOS interface chip are integrated into a low-cost, disposable, lateral flow-based microfluidic architecture.

FIG. 6 shows an exemplary embodiment of a biosensor 60 according to an example embodiment in which a sensor die with a patterned electrochemical interface and CMOS interface chip are integrated into a low-cost, disposable, lateral flow-based microfluidic architecture. In one example use of this embodiment, capillary transport separates serum from whole blood and delivers it to the electrode surface. The biosensor platform comprises elements at the macro-, micro-, and nano-scales, where the microfluidic elements bridge the nano-scale transducer to blood sampling and dispensing at the macro-scale. Since the patterned sensor interface with the integrated electronic is the most expensive component of the platform, the microfluidics is designed such that fabrication costs are low, power consumption is negligible and the microfluidic component can be easily disposed of if excessive blockage obstructs the flow path.

Figure 7:
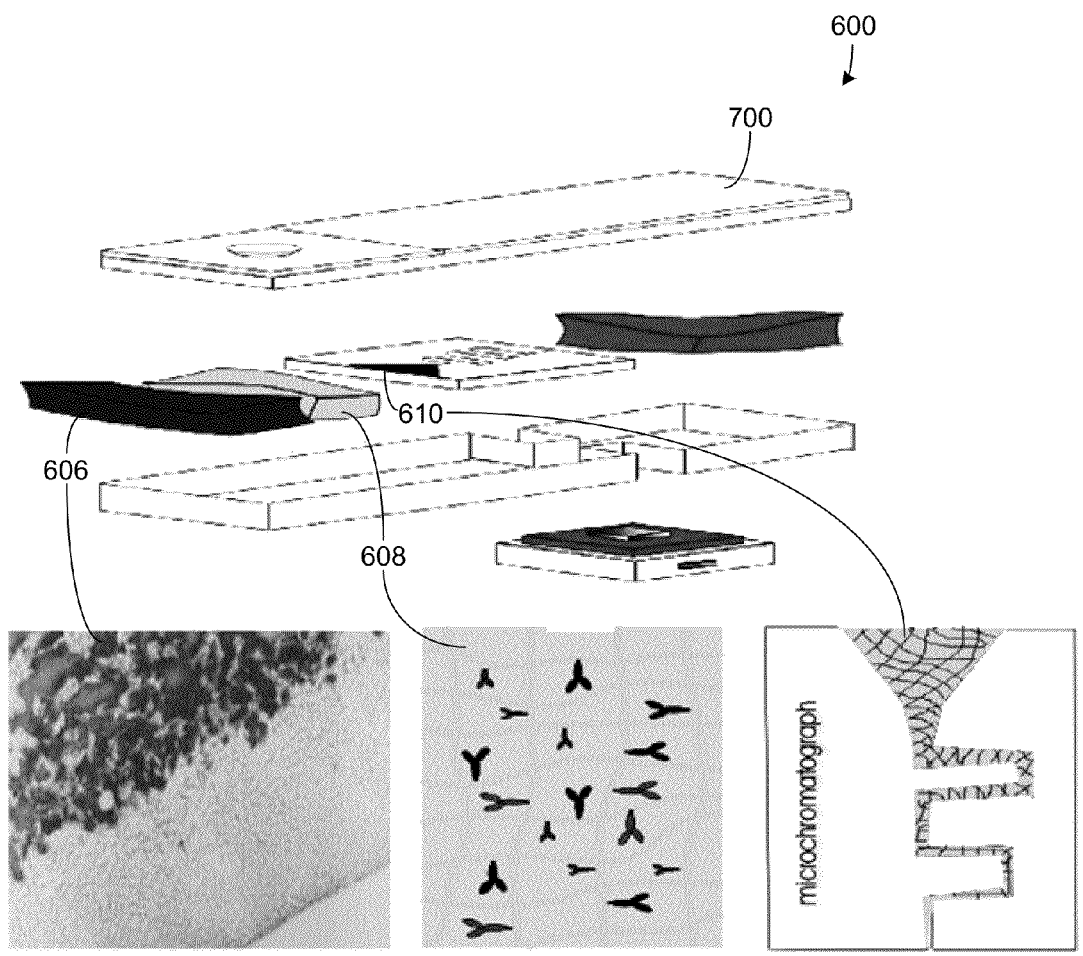
FIG. 7 shows disposable modules that make up a fluidic system for one embodiment of the biosensor.

In FIG. 6, the biosensor 600 comprises an acquisition zone 602, where a sample 604 is dispersed. The sample 604 is then wicked through a modular fluidic system comprising a filtration membrane 606, an immunoseparation membrane 608, a micro-chromatograph column 610, and an adsorption pad 612. With reference to FIG. 7, a disposable module 700 that makes up a fluidic system for one embodiment of the biosensor 600 is illustrated. A sample is first wicked through a filtration membrane 606. In this embodiment, the filtration membrane 606 possesses a graded pore structure capable of separating serum from whole blood. Next the serum passes through an immunoseparation membrane 608, such as a nitrocellulose membrane or other appropriate type of membrane comprising surface antibodies specific to high abundance proteins, which remove the high-abundance proteins. Finally, the liquid sample moves though the micro-chromatograph column 610, thus fractionating the remaining proteins and results in size separated eluants at the column exit. The micro-chromatograph column 610 is comprised of a tapered microfluidic channel containing a photo-polymerized gel.

Although not required for all sample types, a fluidic system module is preferred when analyzing complex mediums, such as blood, where components may interfere with the detection of low abundance analytes. Pumping of the sample may be active or passive into the fluidic system. It should be recognized that the filtration media, chosen filter membranes, other membranes, and characteristics of the micro-chromatography column 610, may be dependent upon factors such as sample, abundance of target analyte, and the like.

Referring back to FIG. 6, after the sample 604 passes through the micro-chromatograph column 610, it passes over the adsorption pad 612 which provides a thermodynamic gradient for passive capillary actuation of the liquid sample. Liquid fractions eluted from the micro-chromatograph column 610 flow over an active sensor interface 614, which comprises a transducing electrochemical interface integrated with underlying acquisition electronics, such as CMOS acquisition electronics. These components are discussed in further detail with reference to FIGS. 8 and 13 below. A sensor area 616 is patterned as electrically accessible, thermally insulated, pixilated electrodes for interrogating the sample 602. It should be appreciated that the sensor pixels 618 can be singular or exist as an array of sensors.

Figure 8:
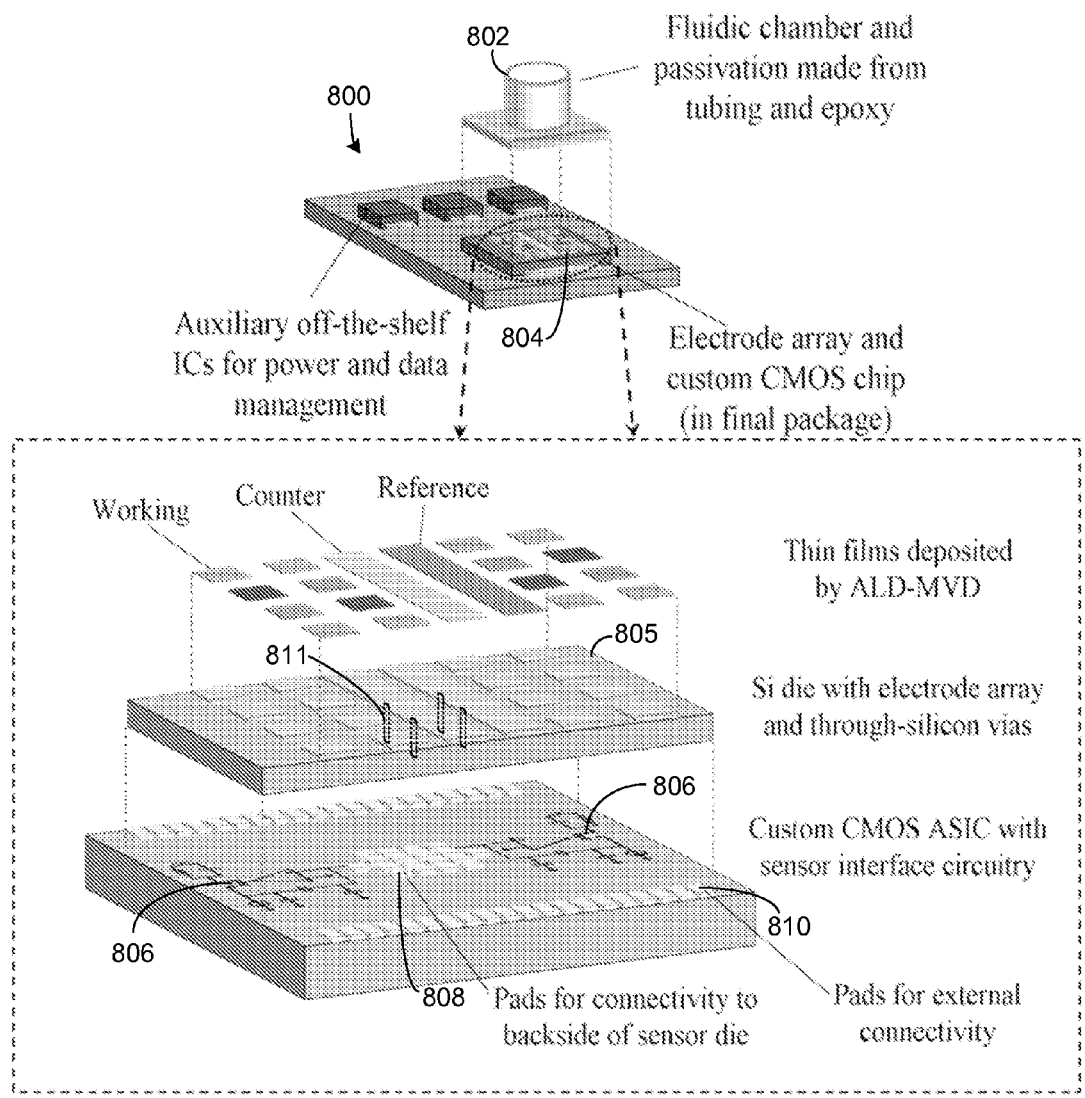
FIG. 8 shows an enlarged view of a sensor package with electrode sensors arranged in an array.

FIG. 8 shows an enlarged view of a sensor package 800 with electrode sensors in arranged in an array. The sensor package 800, in this embodiment, exists as a layered, heterogeneously integrated sensor-CMOS platform. In one embodiment, the sensor package 800 comprises a device 802, which may be at the exit of the column 610 described with reference to FIG. 6, to transfer a liquid sample to the electrode sensor array. The device 802 may be embodied as a fluidic chamber and passivation made from tubing and epoxy, for example.

The sample then reaches an electrode sensor array 804, which comprises, for example, dielectric thin films deposited by Atomic Layer Deposition and/or Molecular Vapor Deposition (ALD-MVD) on a Si die 805 with an electrode array and through-silicon vias 811. In one embodiment, the electrode array 804 is coupled to a CMOS application-specific integrated circuit (ASIC), which further comprises sensor interface circuitry 806. The sensor interface circuitry 806 is described in further detail with reference to FIG. 13. At the level of sensor interface circuitry 806, the device further comprises electronic pads 808 for connectivity to the backside of the sensor die 805 and pads 810 for external device connectivity.

Referring back to FIG. 6, the sensor package is mounted on a shielded printed circuit board (PCB) for electrical access. Parallel data acquisition over a large applied bias range is made possible by electronic-energy-window specific optimization of individual pixels 618, with each pixel nanostructure being optimized for interrogating a specific electronic energy/bias window. Data acquired as one or more transition current signals can be transmitted to an external system 650 for post-acquisition processing, storage, and display. The biosensor platform is designed such that sensing and data acquisition modules can be easily plugged into and out of the fluidic systems, and different elements, such as elements 602, 606, 608, 610, 612, and 614 of the fluidic system exist as modules, so that the platform can be dissembled, interchanged, and disposed of if necessary.

In one embodiment, resolved spectral information, once acquired, is then correlated with vibrational energy data to identify specific molecular species associated with a macromolecule analyte. This may be accomplished by employing an information-driven strategy for targeted, non-redundant analysis of bio-analyte(s) in an electrolyte solution. Signatures of information-rich subsets of a bio-analyte, such as cysteine-containing peptides, phosphorylated peptides, or glycosylated peptides, can be tracked in the resolved spectrum of the bio-analyte. These subsets can serve as molecular markers for identifying and quantifying the presence of the molecular species of interest. A reference database containing these molecular markers can be constructed for each target analyte. In other words, each analyte can produce its own signature spectrum of these information rich subsets. By comparing the resolved spectrum from the sample to the reference database, it is possible to identify the target analyte.

Figure 9:
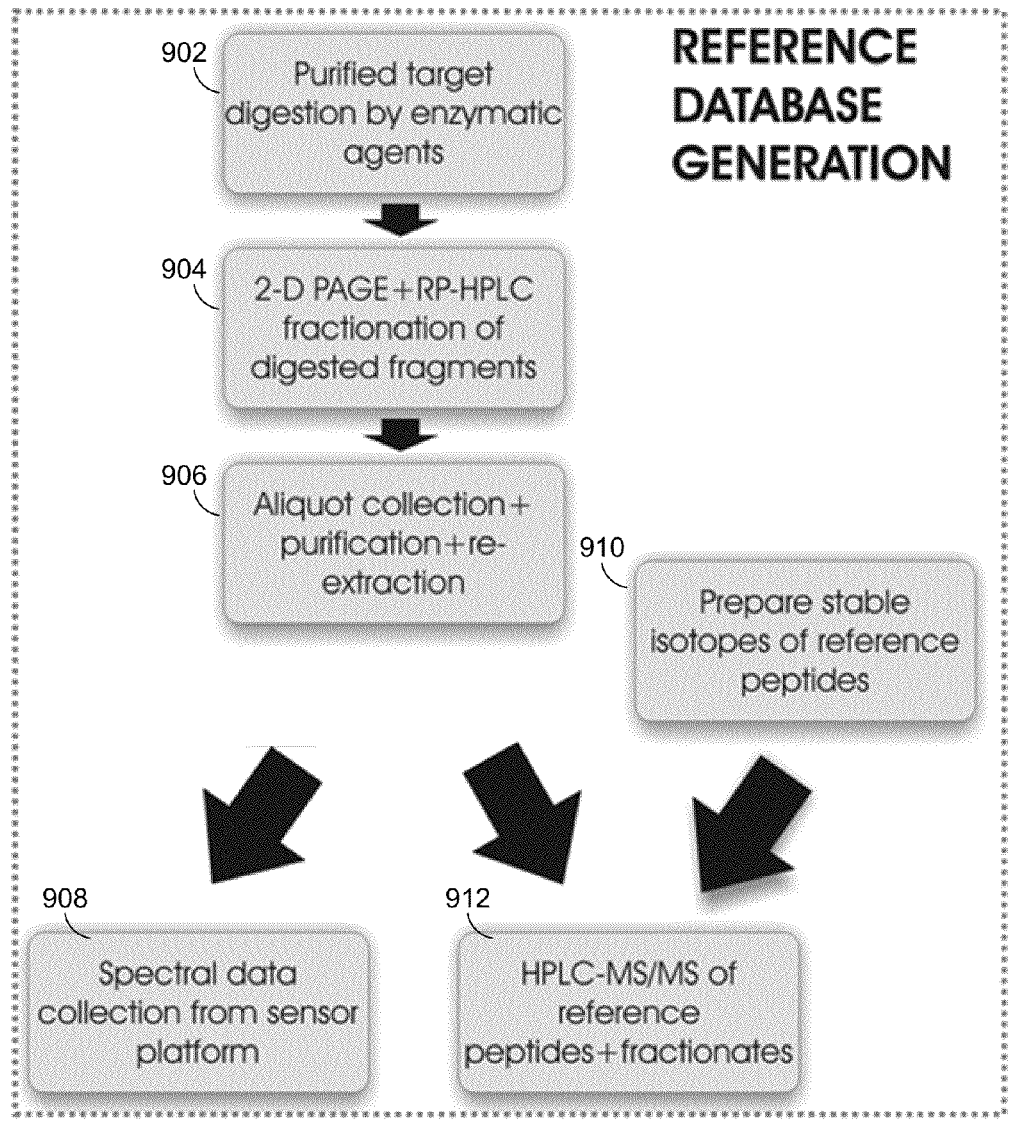
FIG. 9 shows steps in generating a reference database.

FIG. 9 shows steps in generating a reference database. At reference numeral 902, a purified recombinant form of the target molecule (or biological surrogate, in the case of neurotoxins) is systematically digested by enzymes, such as trypsin and chymotrypsin, for example, to generate peptide fragments. This is followed by a three-dimensional separation technique at reference numeral 904, such as 2-D poly acrylamide gel electrophoresis (2-D PAGE) in tandem with high performance liquid chromatography (HPLC), preferably reverse phase-HPLC. Fractions are then collected, purified, and re-extracted in a suitable buffer and analyzed using embodiments of the biosensor or quantum tunneling electronic biosensor described herein at reference numeral 906. The data, after background subtraction, is analyzed for characteristic spectra of moieties specific to the peptide fragment in the aliquot being tested at reference numeral 908. Stable isotopes of reference peptides, for example, may be prepared at reference numeral 910. In some embodiments, the same fractions as well as the isotope-labeled reference peptides prepared at reference numeral 910 may also be examined in parallel by traditional HPLC-MS-MS techniques at reference numeral 912.

Nanoscale Design of the Electrochemical Interface

Figure 10:
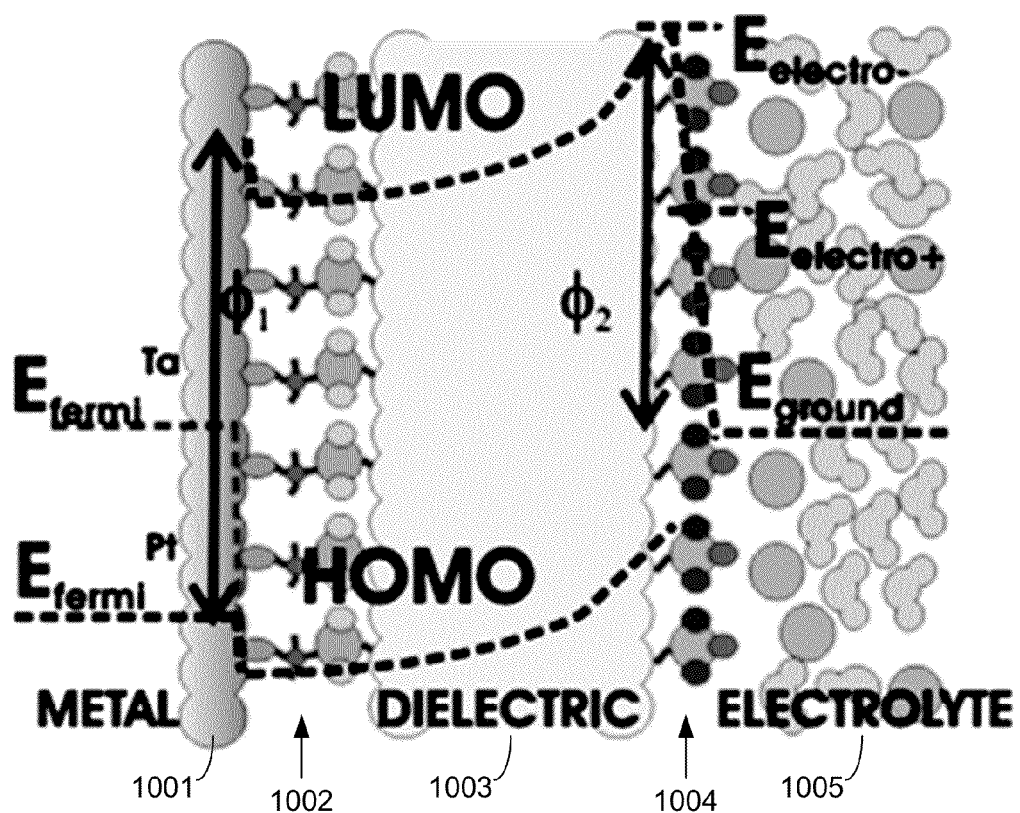
FIG. 10 shows tunneling barriers at metal-dielectric and dielectric-electrolyte interfaces.

For some embodiments, electronic de-coupling is enhanced by configuring the electrochemical interface to minimize overlap between a metal electrode 1001 and electrolyte phase electronic energy surfaces while simultaneously scaling down the transducing surface area. FIG. 10 shows tunneling barriers $\phi_1$ and $\phi_2$ at metal-dielectric 1002 and dielectric-electrolyte 1004 interfaces. Coupling between initial and final electronic energy states in the weakly coupled, non-adiabatic transition is modulated by the electrostatic tunneling barrier $\phi_2$ located at the dielectric-electrolyte interface 1004 as well as by an effective barrier limiting charge injection at the electrode-dielectric interface 1002. Nanoscale engineering of barrier heights at the electrode-dielectric thin-film interface 1002 as well as at the dielectric thin-film-electrolyte interface 1004 is utilized to minimize environmental de-phasing due to electronic coupling.

The desired minimization may be achieved by increasing the electron tunneling barrier $\phi_2$ at the dielectric-electrolyte interface. In one embodiment, the electron tunneling barrier $\phi_2$ is increased by increasing the electrolyte pH. Other exemplary embodiments achieve an increased tunneling barrier by increasing electrolyte anion electronegativity, increasing dielectric monolayer functional group electronegative, and/or increasing dielectric monolayer thickness, for example.

The desired minimization may also be attained by increasing the limiting barrier $\phi_2$ at the dielectric-electrolyte interface 1004. In one embodiment this is achieved by coating the dielectric monolayer 1003 with an organic coating, such as short chain silanes, with different electronegative, electrolyte-facing functional groups, such as —OH, —OR, —COOH, —SH, —SR, —COR, —NO$_2$, —Br, and the like. These aforementioned coatings are suitable for forming with molecular-vapor-deposition at the dielectric surface 1003.

The metal electrode-dielectric barrier 1002, unlike the dielectric-electrolyte barrier 1004, is a function of the metal work-function, dielectric band gap, and nature of molecular orbital distortion induced by a bond between the metal 1001 and dielectric materials 1003. A reduction in the coupling between the electrode 1001 and the electrolyte 1005 may also be achieved by altering the tunneling barrier $\phi_1$ located at the dielectric-electrode interface. For example, increasing the tunneling barrier $\phi_1$ at the dielectric-electrode surface reduces coupling between electrode and electrolyte phases, thus leading to increased resolution of vibrational frequency information in the measured current. For some embodiments, the mechanism of tunneling based charge injection in the dielectric 1003 would be electron tunneling. In other words, the dielectric 1003 would be comprised of an inorganic-oxide. For these embodiments, metals such as Pt, Ir, Se, or Au are preferred. For other embodiments, hole-tunneling is the mechanism of charge injection in the dielectric 1003. One having an ordinary skill would appreciate that the dielectric film 1003 in these embodiments would be comprised of an organic alkane. For these embodiments, metals like Ta, Ti, Zr, or Hf are preferred. The final choice of metal is dependent on many factors including the mechanical, diffusional, and electrochemical stability of the electrode, ease of deposition, electrical resistivity, and ability to seed a dielectric layer, for example.

Figure 11:
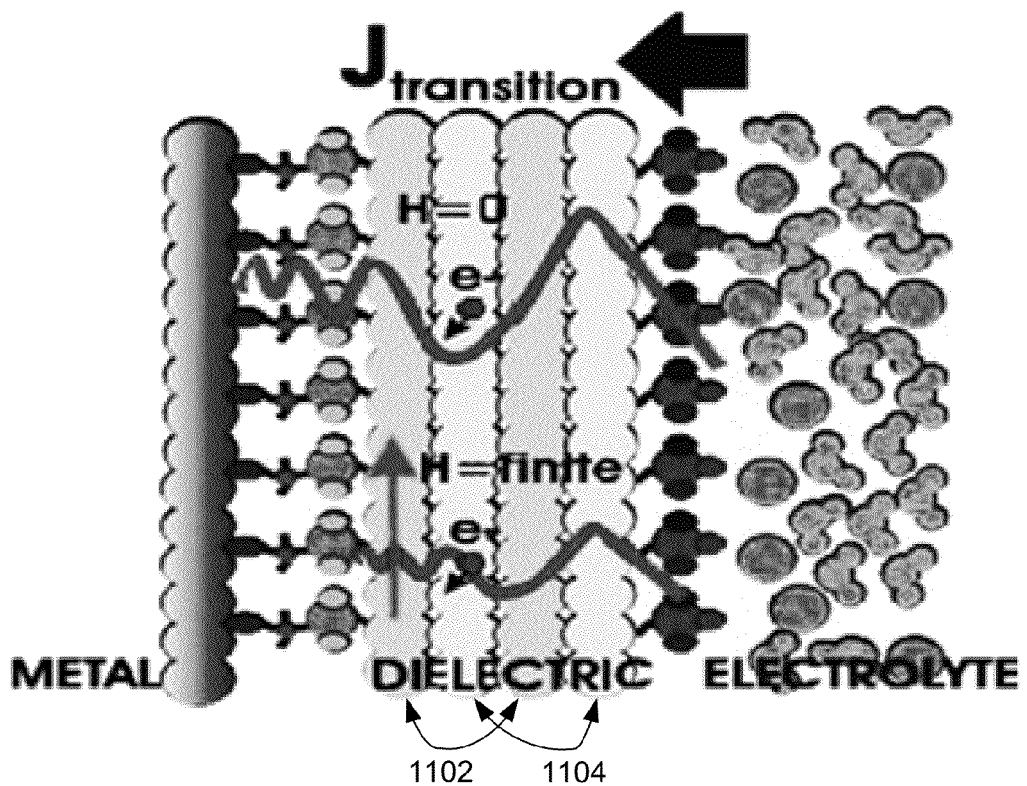
FIG. 11 shows sequential layering of high and low k-dielectric materials for a high-k dielectric insulator.

In various embodiments, the dielectric film 1003 that spatially separates the electrode 1001 and electrolyte 1005 layers is comprised of a high-k, nanolaminate. The high-k material may be Ta$_2$O$_2$, ZrO$_2$, TiO$_2$, or other suitable material. It is noted that large dielectric constants for the insulating film facilitate greater charge accumulation at the dielectric-electrolyte interface, thus effectively increasing the tunneling barrier and reducing coupling. However, a larger dielectric constant is typically associated with a small band-gap and, consequently, higher non-tunneling leakage current. Thus, the high-k material may be intercalated between alternating layers of lower-dielectric constant oxides, such as c or other suitable compound or compounds. In this context, FIG. 11 shows sequential layering of high 1102 and low 1104 k-dielectric materials for a high-k dielectric insulator. The final choice of materials used to form a given dielectric nanolaminate is determined by insulator properties like breakdown resistance, electrochemical and mechanical stability, and chemical inertness to aqueous electrolytes in the presence of an applied bias, for example.

Figure 12:
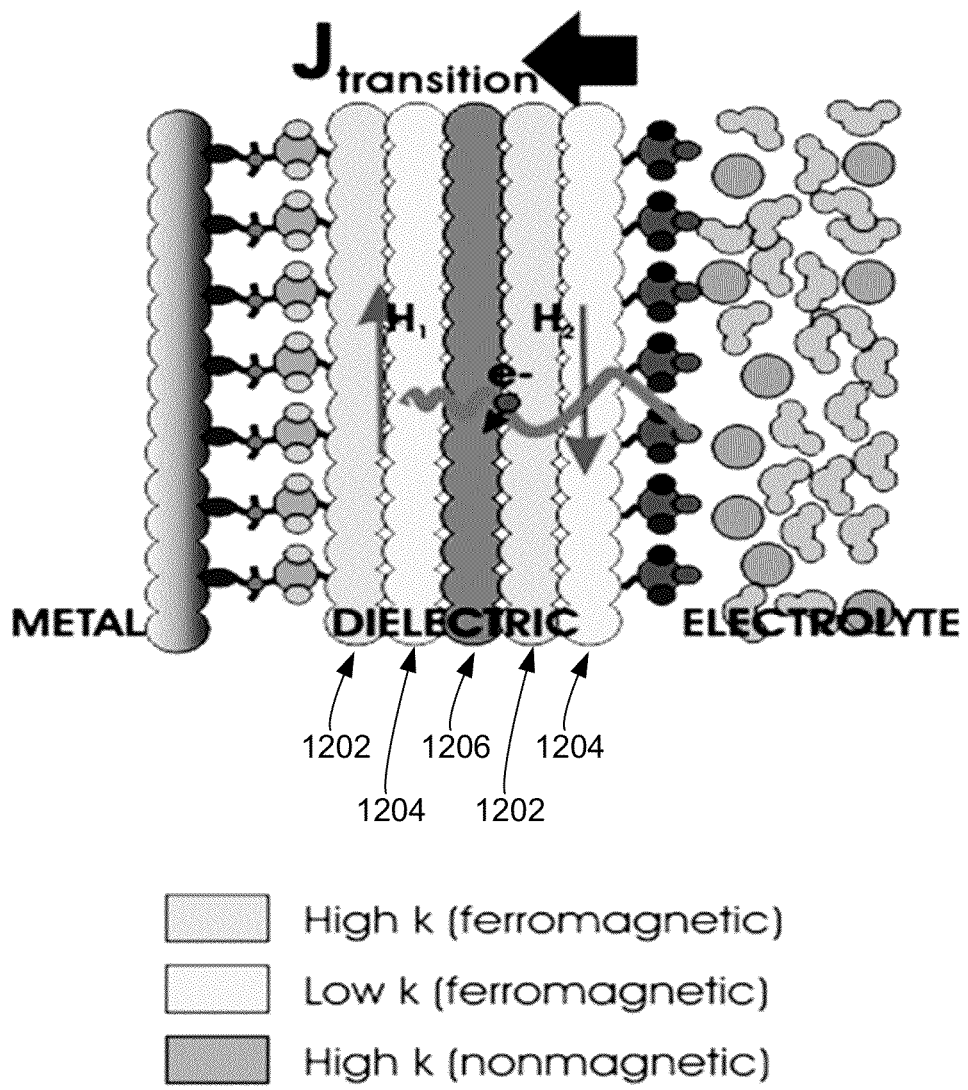
FIG. 12 shows a magnetic tunneling film architecture that uses differentially oriented film magnetic moments to further restrict electronic transition.

Alternatively to mechanical alterations, a reduction in energy state coupling may be achieved by applying a directional magnetic field to the electrochemical interface. In this case, a reduction in coupling may occur by interaction of the magnetic field with a magnetic dipole moment of a transitioning electron, similar to the interaction effect between the applied electric field and charge of the transitioning electron. In various embodiments, a nanolaminate for a dielectric film that relies upon magnetic tunneling uses differentially oriented film magnetic moments to further restrict electronic transition. Preferably, a magnetic tunneling nanolaminate can comprise dielectric-based thin-film architectures with room temperature ferromagnetic properties that allow for the generation of local, inhomogeneous magnetic fields that can interact with the magnetic dipole of the transitioning electron to "gate" the quantum-mechanical transition. In this context, FIG. 12 shows a magnetic tunneling film architecture that uses differentially oriented film magnetic moments to further restrict electronic transition. A multi-stage-gate-like design of the dielectric nanolaminate may enable further minimization of the de-phasing resulting from electronic coupling between the initial and final energy states. In one embodiment, the dielectric film comprises low-k (e.g., $HfO_2$) 1204/ high-k 1202 dielectric substacks interspersed with thin films of a non-magnetic dielectric insulator 1206 with an intermediate value of dielectric permittivity, such as $Al_2O_3$. Aluminum in the $Al_2O_3$ thin-film lack the d-shell orbitals necessary for displaying magnetic susceptibility and thus the alumina thin-films are believed to be non-magnetic, making them suited for this application. In other words, the functional ferromagnetic elements of the dielectric thin film is made up of low-k (e.g., $HfO_2$) 1204/high-k 1202 dielectric substacks and every two subs-stacks are separated by $Al_2O_3$ thin film which functions as an insulating barrier that minimizes conservative and dissipative magnetic coupling between adjoining ferromagnetic sub-stacks. The total number of substacks and $Al_2O_3$ thin films and, thus, the extent of ferromagnetic-induced decoupling, is limited by the overall thickness of the dielectric film, which is less than approximately 10 mm in various embodiments.

Analog Front-End Instrumentation

A key component to the biosensor according to embodiments described herein is analog front-end instrumentation, which is relied upon to achieve minimum noise in an acquired signal. Physical and electronic sources of noise in a measured transition rate limit the extent of decoupling achievable and can become measurement-limiting when transition rates in the weakly-coupled regime are on the order of 10 fA. As stated earlier, scaling down the active electrode area supplements electronic decoupling achieved by engineering the nano-scale, information transducing interface, and simultaneously miniaturizes the sensing platform. Similarly, noise in the system also limits the extent to which the electrode area can be minimized. In sum, to achieve effective device minimization, rapid analyte identification, and battery life preservation, non-electron transfer leakage currents and noise in the acquisition electronics should preferably be minimized.

A measured non-adiabatic current is a function of two non-interacting frequency domains: (a) a "macro-frequency" (approximately 1 Hz) that determines the rate-limiting step in the macroscopic electrochemical system and (b) a "micro frequency" ($>10^{12}$ Hz) that measures the dynamics of molecular vibrations, where the dynamics are manifest in the electronic energy, or applied bias, space. A low-frequency Alternating Current (AC) excitation is applied to the electrochemical interface, and the current is recorded as a function of Direct Current (DC) bias at the electrode. The non-adiabatic transition rate is contaminated, at least in part, by band-limited white noise and electromagnetic interference. Effective signal extraction requires suppression of both extrinsic and intrinsic noise contributions. In short, because of the low frequency transition signal strength, a high signal-to-noise ratio is preferable.

Figure 13:
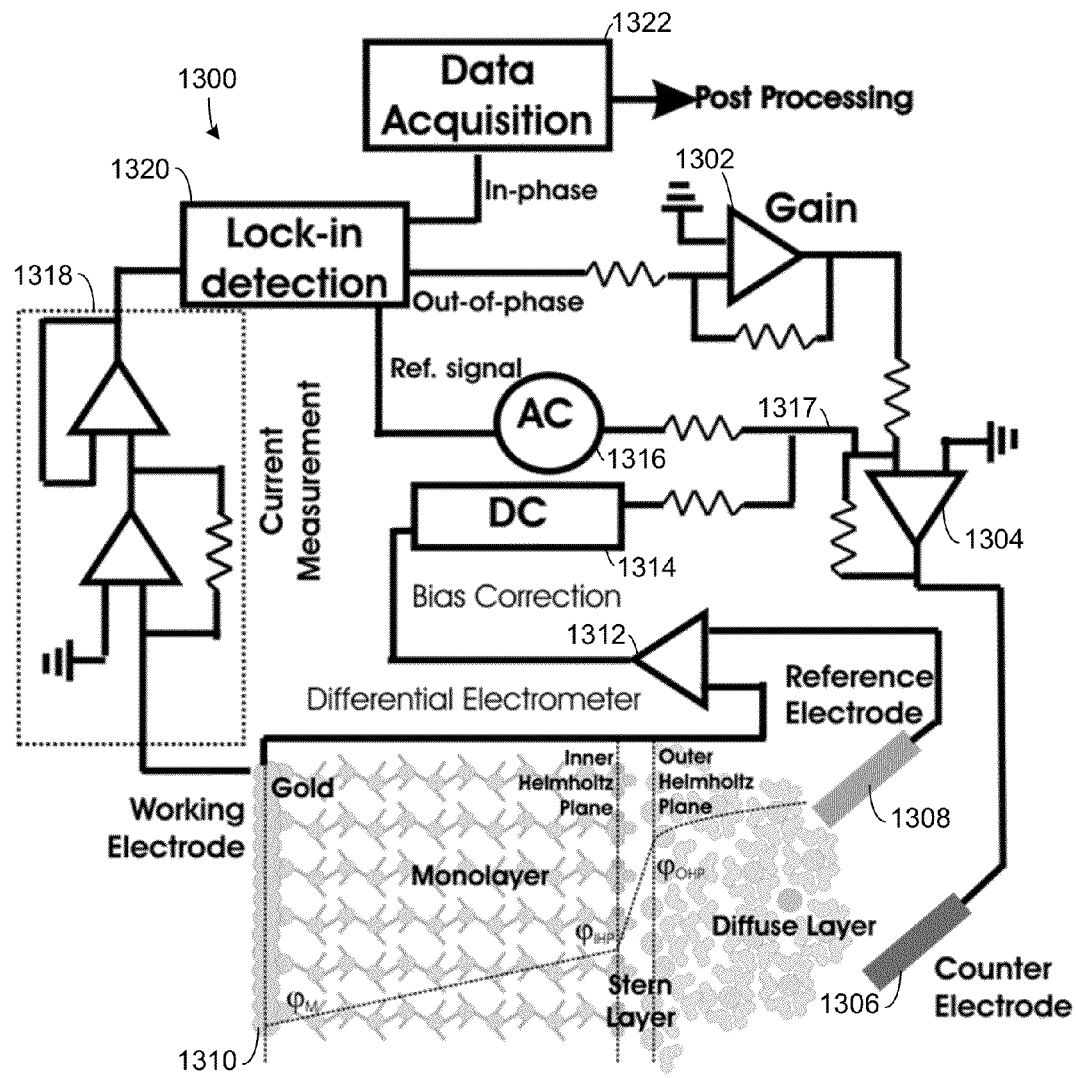
FIG. 13 shows an example of three-electrode feedback suppression of thermal noise for electronic transition measurements.

FIG. 13 shows an example of three-electrode feedback suppression of thermal noise for electronic transition measurements. In one embodiment, a three-electrode analog measurement topology circuit 1300 is used for high gain feedback suppression of voltage-noise in the macro-frequency domain. The circuit 1300 includes a first gain amplifier 1302, a second gain amplifier 1304 coupled to an output of the first gain amplifier 1302, and a counter electrode 1306 coupled to an output of the second gain amplifier 1304. The circuit 1300 further includes a reference electrode 1308 and a working electrode 1310, each coupled to a bias amplifier 1312. An output of the bias amplifier 1312 is coupled to a DC generator 1314. Outputs of the DC generator 1314 and an AC generator 1316 are combined at a node 1317 in the circuit 1300 and provided as an input to the second gain amplifier 1304. As illustrated in FIG. 13, the combined outputs of the DC and AC generators 1314 and 1316 are further combined with the output of the first gain amplifier 1302 at the node 1317 before being provided as input to the second gain amplifier 1304.

The circuit 1300 further includes a current measurement circuit 1318 coupled to the working electrode 1310, and a lock-in detection circuit 1320 coupled to an output of the current measurement circuit 1318. As illustrated in FIG. 13, a reference signal output of the lock-in detection circuit 1320 is provided as an input to the AC generator 1316, an out-of-phase signal output of the lock-in detection circuit 1320 is provided as an input to the first gain amplifier 1302, and an in-phase signal output of the lock-in detection circuit 1320 is provided as an input to a data acquisition element 1322 for processing.

According to one embodiment, a feedback loop of the circuit 1300 acts to minimize thermal noise on the order of 40 $pA/Hz^{1/2}$, at room temperature. In embodiments that have tunneling transition currents on the order of 10 fA, noise on the order of 2 fA rms/$Hz^{1/2}$ would be sufficient for the resolution of spectral features in measured data. In this context, for example, FIG. 14 shows a table containing program metrics.

Sensing of the low frequency modulated energy state transition signal may be performed with low noise current amplification and readout circuitry. The signal acquisition path employs chopper modulation to mitigate flicker noise from CMOS devices, which may be expected to be significant around the "macro" frequency modulation. In one embodiment, a metal-oxide-semiconductor-field-effect transistor (MOSFET) that comprises defect free or substantially defect free oxide interfaces along a channel region is relied upon. This eliminates the trapping and detrapping of carriers that create 1/f noise characteristics.

Although exemplary embodiments have been shown and described, it will be clear to those of ordinary skill in the art that a number of changes, modifications, or alterations to the disclosure as described may be made.

At least the following is claimed:

1. A system for sensing chemical information, the system comprising:
   a fluidic system, comprising:
      a sample acquisition zone;
      a filtration module coupled to the sample acquisition zone;
      an immunoseparation module coupled to the filtration module;
      a tapered micro-chromatogram coupled to the immunoseparation module; and an adsorption pad coupled to the tapered micro-chromatogram; and
a quantum tunneling biosensor interface coupled to the adsorption pad, the quantum tunneling biosensor interface comprising:
  a transducing electrode array comprising dielectric thin films deposited on an electrode array; and
  sensor interface circuitry coupled to the transducing electrode array.

2. A system, comprising:
a quantum tunneling biosensor interface, comprising:
  a transducing electrode array comprising dielectric thin films, the dielectric thin films being layered on a metal electrode array, the metal electrode array being mounted on a silicon die;
  sensor interface circuitry coupled to the transducing electrode array; and
  a voltage source to apply a voltage bias across the transducing electrode array to produce a weakly-coupled non-adiabatic electron flux.

3. The system of claim 2, wherein the sensor interface circuitry is coupled to the transducing electrode array by through-silicon vias in the silicon die.

4. The system of claim 2, further comprising a modular fluidic system, comprising:
  a sample acquisition zone;
  a coarse filtration module coupled to the sample acquisition zone;
  an immunoseparation module coupled to the coarse filtration module;
  a tapered micro-chromatograph coupled to the immunoseparation module; and
  an adsorption pad coupled to the quantum tunneling biosensor interface.

5. The system of claim 4, the quantum tunneling biosensor interface mounted on a shielded printed circuit board.

6. The system of claim 4, the metal electrode array comprising a gold electrode.

7. The system of claim 4, the dielectric thin films comprising a nanolaminate having a high dielectric constant.

8. The system of claim 7, the nanolaminate comprising high dielectric constant layers and low dielectric constant layers, the high dielectric constant layers being intercalated between the low dielectric constant layers.

9. The system of claim 8, the high dielectric constant layers comprising at least one material selected from the group consisting of:
  $HfO_2$;
  $Ta_2O_2$;
  $ZrO_2$; and
  $TiO_2$.

10. The system of claim 8, the low dielectric constant layer comprising an organic alkane layer.

11. The system of claim 4, the dielectric thin films comprising a nanolaminate to apply a directional magnetic field across the transducing electrode array.

12. The system of claim 4, the dielectric thin films comprising layers of a non-magnetic dielectric insulator intercalated between substacks, the substacks comprising alternating layers of a first ferromagnetic material with a high dielectric constant and a second ferromagnetic material with a low dielectric constant.

13. The system of claim 12, the non-magnetic dielectric insulator comprising $Al_2O_3$.

14. A system, comprising:
a quantum tunneling biosensor interface, comprising:
  a transducing electrode sensor array comprising at least one dielectric thin film layered on an electrode array; and
  sensor interface circuitry coupled to the transducing electrode sensor array; and
a fluidic module, comprising:
  a sample acquisition zone;
  an immunoseparation module in fluid communication with the sample acquisition zone; and
  a tapered micro-chromatograph in fluid communication with the immunoseparation module and the quantum tunneling biosensor interface.

15. The system of claim 14, wherein the fluidic module further comprises:
  a coarse filtration module in fluid communication with the sample acquisition zone; and
  an adsorption pad in fluid communication with the tapered micro-chromatograph and the quantum tunneling biosensor interface.

16. The system of claim 14, wherein the transducing electrode sensor array comprises the at least one dielectric thin film layered on a metal electrode array.

17. The system of claim 14, further comprising a voltage source to apply a voltage bias across the transducing electrode sensor array to produce a weakly-coupled non-adiabatic electron flux.

18. The system of claim 14, the at least one dielectric thin film comprising a nanolaminate having a high dielectric constant.

19. The system of claim 14, the at least one dielectric thin film comprising at least one high dielectric constant layer and at least one low dielectric constant layer.

20. The system of claim 19, the at least one high dielectric constant layer comprising a material selected from the group consisting of:
  $Ta_2O_2$;
  $ZrO_2$; and
  $TiO_2$.

* * * * *